United States Patent [19]

Salmon et al.

[11] 3,957,963

[45] May 18, 1976

[54] RADIOIODINATED BLEOMYCIN

[75] Inventors: Sidney E. Salmon; Rosa H. Liu, both of Tucson, Ariz.

[73] Assignee: University Patents, Inc., Stamford, Conn.

[22] Filed: Dec. 3, 1974

[21] Appl. No.: 529,237

[52] U.S. Cl. ................................................. 424/1
[51] Int. Cl.² ........................................ A61K 43/00
[58] Field of Search ........................................ 424/1

[56] References Cited
OTHER PUBLICATIONS

Yamashita et al., Nuclear Science Abstracts, Vol. 27, No. 8, Apr. 30, 1973, Abstract No. 17613.
Grove et al., Nuclear Science Abstracts, Vol. 29, No. 4, Feb. 28, 1974, Abstract No. 8179.
Renault et al., Nuclear Science Abstracts, Vol. 29, No. 11, June 15, 1974, Abstract No. 26740.

*Primary Examiner*—Benjamin R. Padgett
*Assistant Examiner*—Christine M. Nucker
*Attorney, Agent, or Firm*—Mason, Kolehmainen, Rathburn & Wyss

[57] ABSTRACT

Radioiodinated bleomycin is a useful imaging agent for body tissues. Its production by iodination of bleomycin with radioactive iodide ions in the presence of an oxidizing agent is described.

7 Claims, No Drawings

RADIOIODINATED BLEOMYCIN

This invention relates to radioiodinated bleomycin and methods for its production.

BACKGROUND OF THE INVENTION

In recent years much attention has been directed toward the development of radiopharmaceuticals that will concentrate in tumor tissue and permit external imaging of the tumor. Such an approach, if completely successful, would have obvious advantages over other methods currently employed for staging and followup of patients with malignant disease because of the inherent simplicity, lower cost, and low morbidity of scanning techniques. Although an ideal tumor imaging agent has not yet come into routine clinical use, the chance observation that the radionuclide gallium—7 citrate accumulated in soft tissue tumors has led to extensive clinical experience with this particular tumor scanning agent.

Another more rational approach to tumor imaging is to label tumor-specific drugs or antibodies which might selectively concentrate in tumors. The anti-tumor antibiotic bleomycin is such a drug and it has been shown to concentrate in skin, lung, and certain tumors. It has recently been approved for general use on the basis of its demonstrated clinical effectiveness against squamous cell carcimomas, lymphoma, and testicular tumors.

Bleomycin has the desirable characteristic of chelation with a number of bivalent and trivalent cations, such as cobalt, lead, indium and copper. It has thus been possible to chelate radioactive isotopes of such metals to bleomycin and thereby produce radioactive agents which can be used to detect and visualize tumors.

Bleomycin is a mixture of glycopeptide antibiotics discovered by Umezawa et al, in 1962, and isolated from the cultured broth of *Streptomyces verticillus*. It is effective against various animal and human tumors such as squamous cell carcinomas, malignant lymphomas, and testicular tumors. The antibiotic also inhibits the growth of gram positive and gram negative bacteria and appears to bind to cellular DNA.

Thirteen distinct, but closely related, bleomycin peptides have been isolated. They are relatively high molecular weight (ca. 1200), and are known to form metal chelates, as well as being concentrated in tumors.

Bleomycin can be loosely chelated with a wide variety of radionuclides including indium 111, cobalt 57 and lead 203. Studies have been conducted of $^{111}$In-labeled bleomycin as a tumor-imaging agent in patients with a wide variety of neoplasms. The precise mechanism of tumor labeling with $^{111}$In-bleomycin is not fully understood. Although $^{111}$In alone will localize tumors to some extent, the results indicate that tumor localization occurs more frequently with $^{111}$In-labeled bleomycin. However, the radionuclide ($^{111}$In) can dissociate from bleomycin; serum transferrin and the erythroid compartment of the bone marrow both compete with bleomycin for 111In binding. Ionic indium released by bleomycin on dissociation is bound virtually quantitatively to transferrin and accumulated by bone marrow erythroid precursor cells.

A broad spectrum of tumors can be localized with radioactive-labeled bleomycin, despite the lack of therapeutic efficacy of bleomycin alone against these tumors. It appears that two essential steps are involved at the cellular level for bleomycin to exert its oncolytic effect: (a) selective uptake by tumor cells and (b) specific inhibition of DNA synthesis and cell death due to bleomycin's antibiotic effect. Thus, bleomycin can serve as a vehicle for delivering local radioactivity to the target tumor tissue.

$^{111}$In-bloemycin is an important tumor-scanning agent, but it has certain disadvantages. For instance, bleomycin is known to concentrate in the lung and it is possible that diffuse pulmonary uptake of $^{111}$In-bleomycin identifies either those patients with pulmonary damage or those who are susceptible to subsequent development of bleomycin pulmonary toxicity. Another disadvantage is that the $^{111}$In-bleomycin dissociates in body fluids and releases $^{111}$In ions which are absorbed by normal liver and bone marrow which are thereby imaged. Apparently $^{111}$In dissociated from $^{111}$In-bleomycin competes with iron for binding to transferrin and for incorporation into erythroid precursors in the bone marrow.

A tumor-imaging agent should have the following properties: (a) it should be taken up by all malignant tissue in the patient (i.e., highly sensitive); (b) it should not be taken up by any normal or nonmalignant tissues (i.e., highly specific); (c) it should be safe to administer and not give an excessive radiation dose (so that it may be easily and safely employed for serial evaluations); and (d) it should be capable of providing good images with currently available instrumentation (so that only the intrinsic resolution of the instrument would limit the size of the minimally detectable lesion). While clinical data indicate that $^{111}$In-bleomycin is a safe and clinically useful tumor-imaging agent, it is not ideal by these criteria, although it does represent an advance in efforts to develop the ideal radiopharmaceutical.

Lesion detectability is dependent upon two factors: (a) absolute uptake of the agent in question by the tumor and (b) the contrast between the activity present in the tumor and that in adjacent normal tissues. While $^{111}$In-bleomycin is effective in certain areas, there is still need for radioactive scanning agents which are more stable then chelated materials such as $^{111}$In-bleomycin and which are more selective in tissue uptake.

OBJECTS OF THE INVENTION

It is an object of this invention to provide radioactive compounds of bleomycin which are more stable than $^{111}$In-bleomycin complexes.

Another object is to provide methods of producing radioiodine-bleomycin compounds.

An additional object is to provide radioiodinated bleomycin imaging agents for body tissues.

A further object of this invention is to provide radioiodine-labeled bleomycin compounds which in large doses can function as tumor-seeking radiochemotherapeutic anticancer drugs.

GENERAL DESCRIPTION OF THE INVENTION

We have discovered that bleomycin labeled with radioactive iodine is more stable than $^{111}$In-labeled bleomycin. The radioiodine is attached to the tetrapeptide of bleomycin and does not dissociate in aqueous fluids as do metal ions which are chelated to the bleomycin molecule, such as copper, cobalt and indium.

We have also discovered that radioiodinated bleomycin is attracted to tumor tissue in animals and humans and in this way delivers a highly radioactive isotope, radioiodine, specifically to such tissue. It thus serves as a scanning agent for imaging and locating tumor tissue in the body.

We have further discovered procedures for producing radioiodinated bleomycin which are not destructive of the bleomycin and do not interfere with its antibiotic activity.

The location of radioiodinated bleomycin in the body can be determined by scanning with a dual-probe rectilinear scanner, a multi-channel analyzer, a gamma camera, or scintillation camera. By this procedure the tissue in which the radioiodinated bleomycin has localized can be visualized and identified.

The radioactive isotopes of iodine used in preparing the radioiodinated bleomycin have relatively short half lives (13.3 hours to 60 days) in contrast to radioactive cobalt (270 days). These shorter half lives avoid the disadvantages of routine collection and storage of urine of patients for the first two days after administration.

In accordance with our invention, bleomycin in a buffer solution at neutral pH is reacted at low temperature with carrier-free NaI, wherein the I is $I^{123}$, $I^{125}$ or $I^{131}$, in the presence of an oxidizing agent such as chloramine-T or hydrogen peroxide-lactoperoxidase. After the reaction the excess of NaI is removed, preferably with ion-exchange glass beads or an ion-exchange gel resin which absorbs ions but not the radioiodinated bleomycin. The latter can be used in the aqueous solution in which it is isolated, or can be separated therefrom and purified by known techniques used for the isolation and purification of bleomycin.

The amount of radioiodine introduced into the bleomycin can vary substantially. The amount need only be sufficient for scanning with available instruments. The practical range is 0.1 to 5 millicuries of radioiodine per milligram of bleomycin. In practice 1-3 millicuries/mg is desirable; this level is adequate for both diagnostic and therapeutic use of idobleomycin. $^{125}I$-bleomycin is stable for at least one month. $^{123}I$-bleomycin has excellent imaging properties and a short half-life (13.3 hours).

The dosage level of the radioiodinated bleomycin is less than 0.5 milligram per square meter of body surface area, usually 0.2 to 0.3 mg per m², although dosages up to 15 mg/m² can be administered.

The invention is disclosed in further detail by the following examples. Three isotopes of iodine ($I^{123}$, $I^{125}$ and $I^{131}$) were utilized for labeling of bleomycin. $I^{125}$ has a long (60-day) half-life and is preferred for long shelf life, whereas $I^{123}$ and $I^{131}$ have shorter halflives which are valuable in external scanning.

The radioiodination of bleomycin is conducted in aqueous solution at pH from about 6.5 to 7.5, preferably in a buffered solution, at low temperature in the range from 0° to about 20°C. The radioiodine is supplied as one of the following radioiodide ions: $^{123}I^-$, $^{125}I^-$, or $^{131}I^-$. The radioiodination occurs in the presence of an oxidizing agent such as chloramine-T or hydrogen peroxidelactoperoxidase in a relatively short time (10–40 minutes). The reaction mixture can be passed through ion-exchange resin or gel to remove radioiodide ions and other anions or cations to produce an aqueous solution of radioiodinated bleomycin suitable for parenteral administration.

EXAMPLE 1

Iodination with Chloramine-T

Bleomycin was subjected to iodination with

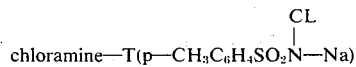

chloramine—T(p—$CH_3C_6H_4SO_2N$—Na)

A reaction vial containing 0.1 ml of 0.15 molar tris-saline buffer (pH 7.4) was chilled to 0°C and kept on ice in a chemical hood. The following reagents were added with shaking: 1 mCi of carrier-free $NaI^{125}$ in 0.1 ml of buffer, 5 µl of 0.02 M zinc sulfate solution in buffer, 0.25 mg of bleomycin sulfate in 0.25 ml of buffer, and 0.75 mg of chloramine-T in 0.25 ml of buffer. The reaction mixture was shaken vigorously for 15 minutes while maintained at ice temperature, after which time 0.75 mg of sodium metabisulfite in 0.25 ml of tris-saline buffer was added to stop the reaction. The reaction vial was shaken for an additional 5 minutes and then transferred to an ion-exchange resin gel chromatographic column (Sephadex G-50, bed volume 40 mls) equilibrated with 0.5% bovine serum albumin (BSA-Sigma Chemicals, St. Louis) to remove free $I^{125}$ from the labeled bleomycin. Elution was carried out with 80 mls of tris-saline solution containing 0.5% BSA. By this procedure, an aqueous solution of $^{125}I$-bleomycin was produced which, after sterilization, was suitable for administration to humans and animals. Column monitoring was carried out both with measurement of absorbency of bleomycin at 280 nanometers, and by radioactivity counting with an automatic gamma counter.

EXAMPLE 2

Enzymatic Iodination with Lactoperoxidase

Iodination of bleomycin by the lactoperoxidase technique was performed at 23°C, in a 5-ml reaction vial. Reagents were added in the following order and amounts: 1.0 mCi of carrier-free $NaI^{125}$ in 0.1 ml water, 5 µl of 0.02 M zince sulfate solution in water, 0.25 mg of bleomycin (in 0.05 ml of double distilled water), 0.2 mg (40-45 units of activity/mg) of lactoperoxidase dissolved in 0.08 ml of 0.15 molar tris-saline solution, and 0.01 ml of 30% $H_2O_2$ solution. After vigorous shaking for 20 minutes, 0.2 ml of tris-saline buffer was added, and the reaction mixture transferred to a Sephadex-G50 column as described in Example 1. The eluate of the lactoperoxidase peak (which elutes in the void volume) was discarded, and the labeled bleomycin peak eluate was pooled and stored at −20°C.

EXAMPLE 3

Measurement of Bleomycin Biological Activity

*Bacillus subtilis* was used as a test organism for measurements of bleomycin antibiotic with disc and turbidity assays. For the disc assay, the test organism was plated uniformly on Muller-Hinton nutrient plates. Samples of bleomycin (both standards and iodinated preparations) were quantitatively absorbed onto 6-mm Whatman No. 1 filter paper discs which were placed on the surface of the nutrient agar plates. After overnight incubation of the plates at 37°C, ring diameters of the zones of inhibition of bacterial growth around the discs were measured, and standard curves for bleomycin concentration constructed from measurements of ring diameters produced by known concentrations of unlabeled bleomycin. For the more rapid turbidity assay, a series of nutrient broth tubes were prepared containing various concentrations of unlabeled bleomycin standards or radioiodinated bleomycin preparations. A standard innoculum of *Bacillus subtilis* was added to each tube, and the samples incubated in a water bath at 37°C for 3 hours. The turbidity of the bacterial suspensions were then measured with a spectrophotometer (500 nanometers), and standard concentration curves constructed.

EXAMPLE 4

Distribution of $I^{125}$ bleomycin in normal rat tissues 0.05 ml of a saturated KI solution was injected subcutaneously into 200-g Sprague-Dawley rats. One hour later, 100 micrograms of $I^{125}$ bleomycin (500,000 cpm) was injected intravenously. Following a 1-hour distribution time, rats were sacrificed, and kidney, heart, tongue, skin, liver, and lung were removed, minced, homogenized and aliquoted for radioactivity counting and measurement of bleomycin antibiotic activity. Tissues from rats injected only with KI and non-radioactive bleomycin served as controls for these experiments.

We claim:

1. Radioiodinated bleomycin, wherein the radioiodine is selected from the group consisting of $I^{123}$, $I^{125}$ and $I^{131}$.

2. Radioiodinated bleomycin as defined by claim 1, wherein the radioiodinated bleomycin contains about 0.1 to about 5 millicuries of radioiodine per milligram of bleomycin.

3. Method of producing radioiodinated bleomycin which comprises reacting bleomycin in aqueous solution with radioiodide ion in the presence of an oxidizing agent and then separating the radioiodinated bleomycin from the excess of radioiodide ion to produce an aqueous solution of radioiodinated bleomycin.

4. Method of claim 3 wherein the radioiodide ion is selected from the group consisting of $^{123}I^-$, $^{125}I^-$ and $^{131}I^-$.

5. Method of claim 4 wherein the aqueous solution of bleomycin is maintained at a pH of 6.5 to 7.5.

6. Method of claim 5 wherein the oxidizing agent is selected from the group consisting of chloramine-T and hydrogen peroxide.

7. Method of claim 5 wherein the excess of radioiodide ion is removed by ion exchange.

* * * * *